US00PP27468P3

(12) United States Plant Patent
Kinney

(10) Patent No.: US PP27,468 P3
(45) Date of Patent: Dec. 20, 2016

(54) ***TSUGA* PLANT NAMED 'MONJERS'**

(50) Latin Name: *Tsuga canadensis*
Varietal Denomination: MonJers

(71) Applicant: Ron D. Kinney, Dayton, OR (US)

(72) Inventor: Ron D. Kinney, Dayton, OR (US)

(73) Assignee: Monrovia Nursery Company, Azusa, CA (US)

( * ) Notice: Subject to any disclaimer, the term of this patent is extended or adjusted under 35 U.S.C. 154(b) by 88 days.

(21) Appl. No.: 14/544,804

(22) Filed: Feb. 22, 2015

(65) Prior Publication Data

US 2016/0249509 P1 Aug. 25, 2016

(51) Int. Cl.
*A01H 7/00* (2006.01)

(52) U.S. Cl.
USPC ..... Plt./213

(58) Field of Classification Search
USPC ..... Plt./213
See application file for complete search history.

*Primary Examiner* — June Hwu
(74) *Attorney, Agent, or Firm* — Cassandra Bright

(57) ABSTRACT

A new and distinct *Tsuga* cultivar named 'MonJers' is disclosed, characterized by distinctive Yellow-Orange winter foliage. Plants have a distinctive upright, pyramidal growth habit. The new cultivar is a *Tsuga*, suitable for ornamental garden purposes.

1 Drawing Sheet

Latin name of the genus and species: *Tsuga canadensis.* Variety denomination: 'MonJers'.

BACKGROUND OF THE INVENTION

The new cultivar is a product of a breeding program under the direction of the inventor, Ron D. Kinney. This new variety, hereinafter referred to as 'MonJers', was selected from seedlings resulting from the collection of seed from an unnamed, unpatented *Tsuga canadensis*. The pollen parent is unknown. The novel seedling was discovered in a commercial nursery in Dayton, Oreg. during December of 2011.

After identifying the new variety as a potentially interesting selection, the inventor first organized propagation of 'MonJers' by semi-hardwood cuttings at the same commercial nursery during November of 2012. The inventor continued controlled testing and propagation, assessing stability of the unique characteristics of this variety. At least four generations have been reproduced and have shown that the unique features of this cultivar are stable and reproduced true to type.

SUMMARY OF THE INVENTION

The cultivar 'MonJers' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MonJers' These characteristics in combination distinguish 'MonJers' as a new and distinct *Tsuga* cultivar:

1. Unique color of foliage: Winter foliage is colored near Yellow-Orange 18A.
2. Distinctive upright, pyramidal and arching growth habit.

COMPARISON TO PARENT VARIETY

'MonJers' is similar in most horticultural characteristics to the seed parent variety. Plants of the new cultivar 'MonJers' however, produce distinctive foliage colored near Yellow-Orange 18A in the Winter months. Additionally the plant habit of 'MonJers' is upright and pyramidal, whereas the parent variety has a plant habit that is compact and flattened.

COMMERCIAL COMPARISON

In addition to the seed parent, 'MonJers' can be compared to the commercial variety *Tsuga canadensis* 'Emerald King', unpatented. The varieties are similar in most horticultural characteristics, however, plants of 'MonJers' produce Winter foliage colored near Yellow-Orange 18A, whereas plants of 'Emerald King' remain green.

'MonJers' can be compared to the commercial variety *Tsuga canadensis* 'MonKinn', U.S. Plant Pat. No. 25,503. The varieties are similar in most horticultural characteristics, however, plants of 'MonJers' are upright and pyramidal, whereas plants of 'MonKinn' are compact and flattened.

BRIEF DESCRIPTION OF THE PHOTOGRAPH

The accompanying photograph in FIG. 1 illustrates in full color a typical plant of 'MonJers' grown outdoors in Dayton, Oreg. The plant is approximately 2 years old, and is shown in a three gallon container. The plant of 'MonJers' is on the left side of the photograph. The plant on the right side is the comparator, 'MonKinn'.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MonJers' plants grown outdoors in Dayton, Oreg. Plants are approximately 2 years old, in a 3 gallon nursery container. Measurements and numerical values represent averages of typical plant types.

Botanical classification: *Tsuga canadensis* 'MonJers'.

PROPAGATION

Time to rooting: 60 to 90 days at approximately 40-50° F.

Root description: Fibrous, very well branched. Colored near RHS Brown 200C.

PLANT

Growth habit: Upright pyramidal with arching branches.

Height: Approximately 75 cm. after 2 years.

Plant spread: Approximately 70 cm. after 2 years.

Typical growth rate: Moderate for species.

Pinching required: No.

Branching characteristics: Single main stem with approximately 20 to 25 lateral branches. Lateral stems are held at an angle of approximately 45 to 30 degree from the main stem. With maturity these main lateral branches develop a slight downward arch at approximately last 30% to 50% of branch. Main lateral branches have between 10 and 15 secondary branches each.

Length of lateral branches: Average 40 cm.

Average number of lateral branches: Approximately 20 to 25 main lateral branches, each with between 10 and 15 secondary lateral branches.

Diameter of lateral branches: Average 0.5 cm.

Lateral branch shape in cross section: Generally round.

Lateral branch strength: Flexible.

Lateral branch color: Near RHS Greyed-Orange 177B.

Lateral branch texture: Rough with hard, protruding lenticels. Younger branches do not have lenticels, texture is striated.

Internode length: Average range between 1.0 and 2.0 cm.

Lenticels:

*Shape*.—Round.

*Average length*.—Approximately 0. cm.

*Average width*.—Approximately 0.15 cm.

*Color*.—Near RHS Greyed-Green 197C.

FOLIAGE

General description: Tightly held, scale like leaves on planar branchlets.

Leaf:

*Arrangement*.—Alternate. Somewhat spiral attachment, however, most foliage occurs on a single, flattened plane.

*Type*.—Flattened, nearly needlelike.

*Shape of blade*.—Linear.

*Average length*.—Approximately 1.0 cm.

*Average width*.—Approximately 0.25 cm.

*Apex*.—Acute.

*Base*.—Obtuse.

*Attachment*.—Sessile.

*Margin*.—Entire.

*Texture of top surface*.—Glabrous.

*Texture of bottom surface*.—Glabrous.

*Leaf internode length*.—Approximately 0.1 cm.

*Color*.—Young foliage upper side: Near RHS Green 138A. Young foliage under side: Near RHS Green 138B. Mature foliage upper side: Near RHS Green 137B. Mature foliage under side: Near RHS Green 137D. Winter Foliage: Upper side: Near RHS Yellow-Orange 18A. Under side: Near RHS Yellow-Green 144A, streaked almost entirely with Yellow-Orange 18A.

*Venation*.—Linear, indistinguishable from leaf blade.

*Durability of foliage to stresses*.—Flexible and resistant to breakage.

*Fragrance*.—Mild, pleasant cedar to pine like scent.

FLOWER

Flowering not observed.

OTHER CHARACTERISTICS

Disease and pest resistance: Neither resistance nor susceptibility observed.

Drought tolerance: No tolerance for drought.

Temperature tolerance: USDA Zones 4-8.

What is claimed is:

1. A new and distinct cultivar of *Tsuga* plant named 'MonJers' as herein illustrated and described.

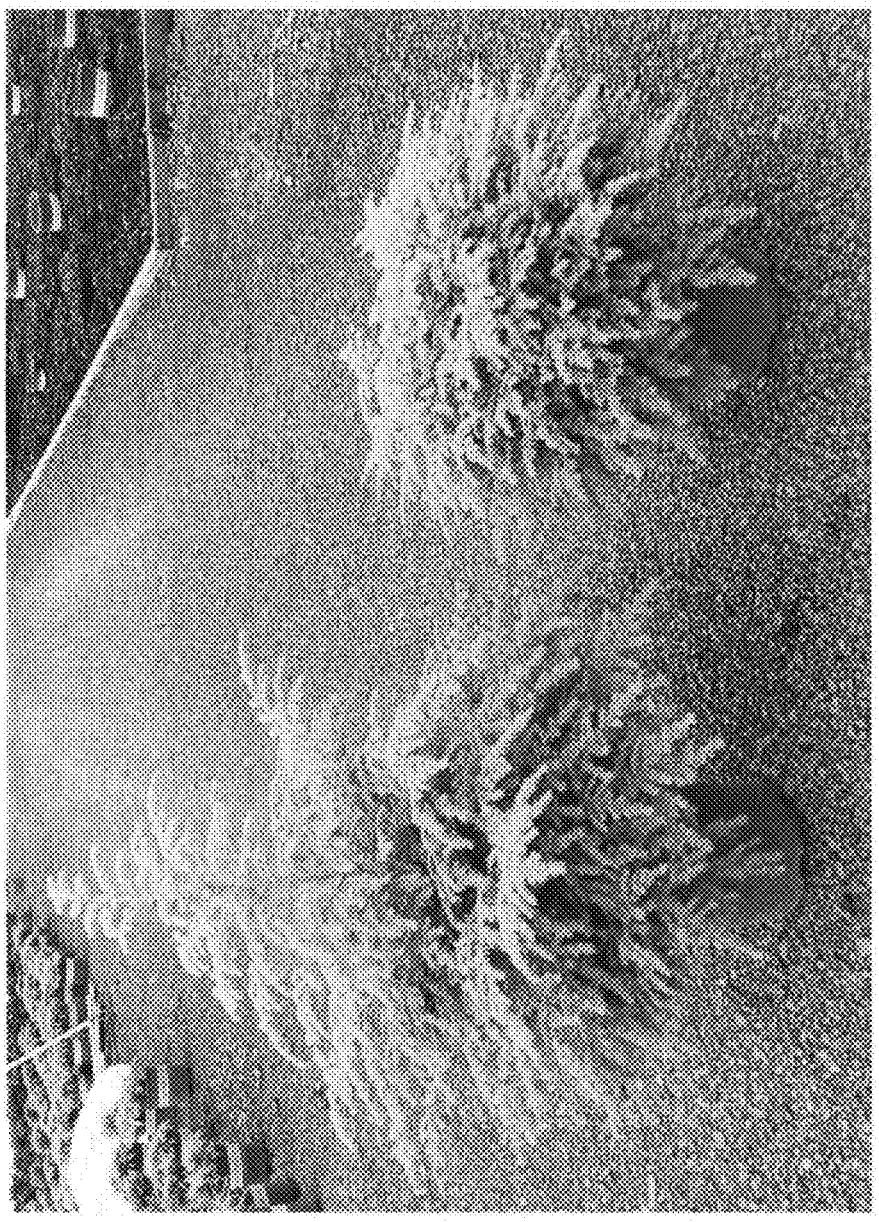

* * * * *